(12) United States Patent
Chen et al.

(10) Patent No.: US 8,062,755 B2
(45) Date of Patent: *Nov. 22, 2011

(54) SURFACE MODIFICATION OF ELASTOMERIC ARTICLES

(75) Inventors: Seong Fong Chen, Penang (MY); Chaung Sim Chong, Penang (MY); Wei Cheong Wong, Kedah (MY)

(73) Assignee: Allegiance Corporation, McGaw Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/487,293

(22) Filed: Jun. 18, 2009

(65) Prior Publication Data

US 2009/0255033 A1    Oct. 15, 2009

Related U.S. Application Data

(63) Continuation of application No. 10/666,650, filed on Sep. 17, 2003, now Pat. No. 7,566,502.

(51) Int. Cl.
B32B 25/20    (2006.01)
(52) U.S. Cl. ........................ 428/447; 428/451
(58) Field of Classification Search ............ 428/447, 428/451
See application file for complete search history.

(56) References Cited

U.S. PATENT DOCUMENTS

| | | | |
|---|---|---|---|
| 4,310,928 A | 1/1982 | Joung |
| 4,442,133 A | 4/1984 | Greco et al. |
| 4,499,154 A | 2/1985 | James et al. |
| 4,548,844 A | 10/1985 | Podell et al. |
| 4,575,476 A | 3/1986 | Podell et al. |
| 4,576,476 A | 3/1986 | Marshall, II et al. |
| 4,675,347 A | 6/1987 | Mochizuki et al. |
| 4,853,978 A | 8/1989 | Stockum |
| 5,030,659 A | 7/1991 | Bansemir et al. |
| 5,089,205 A | 2/1992 | Huang et al. |
| 5,133,090 A | 7/1992 | Modak et al. |
| 5,261,421 A | 11/1993 | Milner |
| 5,284,607 A | 2/1994 | Chen |
| 5,335,373 A | 8/1994 | Dresdner et al. |
| 5,395,666 A | 3/1995 | Brindle |
| 5,405,666 A | 4/1995 | Brindle |
| 5,487,896 A | 1/1996 | Modak et al. |
| 5,534,350 A | 7/1996 | Liou |
| 5,545,451 A | 8/1996 | Haung et al. |
| 5,567,341 A | 10/1996 | Tury |
| 5,616,338 A | 4/1997 | Fox, Jr. et al. |
| 5,736,251 A | 4/1998 | Pinchuk |
| 5,742,943 A | 4/1998 | Chen |
| 5,776,430 A | 7/1998 | Osborne et al. |
| 5,792,531 A | 8/1998 | Littleton et al. |
| 5,827,870 A | 10/1998 | Chodosh |
| 5,881,387 A | 3/1999 | Merovitz et al. |
| 5,888,441 A | 3/1999 | Milner |
| 5,906,823 A | 5/1999 | Mixon |
| 5,951,993 A | 9/1999 | Scholz et al. |
| 5,993,839 A | 11/1999 | Mixon |
| 5,993,923 A | 11/1999 | Lee |
| 5,993,972 A | 11/1999 | Reich et al. |
| 6,012,169 A | 1/2000 | Nishi et al. |
| 6,016,570 A | 1/2000 | Vande Pol et al. |
| 6,019,922 A | 2/2000 | Hassan et al. |
| 6,037,386 A | 3/2000 | Modak et al. |
| 6,046,144 A | 4/2000 | Karol et al. |
| 6,051,320 A | 4/2000 | Noecker et al. |
| 6,075,081 A | 6/2000 | Nile et al. |
| 6,087,400 A | 7/2000 | Dyer et al. |
| 6,195,805 B1 | 3/2001 | Bourne et al. |
| 6,198,805 B1 | 3/2001 | Jambunathan et al. |
| 6,254,947 B1 | 7/2001 | Schaller et al. |
| 6,306,514 B1 | 10/2001 | Weikel et al. |
| 6,347,408 B1 | 2/2002 | Yeh |
| 6,347,409 B1 | 2/2002 | Nile et al. |
| 6,352,666 B1 | 3/2002 | Nile et al. |
| 6,352,791 B1 | 3/2002 | Fink et al. |
| 6,358,557 B1 | 3/2002 | Wang et al. |
| 6,378,137 B1 | 4/2002 | Hassan et al. |
| 6,383,552 B1 | 5/2002 | Noecker et al. |
| 6,391,409 B1 | 5/2002 | Yeh et al. |
| 6,440,498 B2 | 8/2002 | Schaller |
| 6,465,521 B1 | 10/2002 | Rosenberg |
| 6,488,948 B1 | 12/2002 | Danieli |

(Continued)

FOREIGN PATENT DOCUMENTS

EP    0 852 148    2/2002

(Continued)

OTHER PUBLICATIONS

L. Ray Calhoun et al.; "Electron-Beam Systems for Medical Device Sterilization"; Medical Plastics and Biomaterials; Jul./Aug. 1997; p. 26-31.

*Primary Examiner* — Kuo-Liang Peng
(74) *Attorney, Agent, or Firm* — Arent Fox, LLP

(57) ABSTRACT

The invention disclosed herein relates to improved elastomeric articles and processes for making the elastomeric articles. In particular, the invention relates to the surface modification of elastomeric articles such as industrial, surgical, and examination gloves that provides for improved consistency with respect to surface tack on a single article, between different articles from a single production batch, and between articles from separate production batches. The surface modification treatment comprises application of an aqueous mixture of silicone emulsion and ammonium salts of alkyl phosphates to the surfaces of elastomeric articles.

12 Claims, No Drawings

U.S. PATENT DOCUMENTS

| | | |
|---|---|---|
| 6,503,952 B2 | 1/2003 | Modak et al. |
| 6,566,408 B1 | 5/2003 | Cotrell et al. |
| 7,566,502 B1 * | 7/2009 | Chen et al. .......... 428/451 |
| 2001/0053421 A1 | 12/2001 | Schaller |
| 2002/0005812 A1 | 1/2002 | Kuo et al. |
| 2002/0009561 A1 | 1/2002 | Weikel et al. |
| 2002/0029402 A1 | 3/2002 | Yeh |
| 2002/0041899 A1 | 4/2002 | Chudzik et al. |
| 2002/0054910 A1 | 5/2002 | Ronchi et al. |
| 2002/0103333 A1 | 8/2002 | Honeycutt |
| 2002/0160029 A1 | 10/2002 | Asmus et al. |
| 2002/0173563 A1 | 11/2002 | Wang et al. |
| 2002/0173775 A1 | 11/2002 | Modak et al. |
| 2002/0176879 A1 | 11/2002 | Dodd et al. |
| 2004/0126604 A1 | 7/2004 | Wang et al. |

FOREIGN PATENT DOCUMENTS

| | | |
|---|---|---|
| WO | WO 92/13497 | 8/1992 |
| WO | WO 00/47070 | 8/2000 |
| WO | WO 02/32475 A2 | 4/2002 |
| WO | WO 02/41869 | 5/2002 |
| WO | WO 02/055055 | 7/2002 |
| WO | WO 02/055060 | 7/2002 |

* cited by examiner

SURFACE MODIFICATION OF ELASTOMERIC ARTICLES

CROSS-REFERENCE TO RELATED APPLICATION

This application is a Continuation of U.S. patent application Ser. No. 10/666,650, filed on Sep. 17, 2003, now Patent No. 7,566,502 issued on Jul. 28, 2009, the disclosure of which is hereby incorporated in its entirety by reference.

BACKGROUND OF THE INVENTION

Powder free gloves have been produced by using powder free coating technology in combination with chlorination or other post treatment processes. Some of these coated gloves use a manufacturing process which requires that the substrate be treated with acid or other harsh chemicals to improve adhesion of the coating to the base rubber glove. This additional chemical processing step is not preferable in glove manufacturing because the chemicals used are generally corrosive and/or difficult to handle in large scale production processes. Additionally, most of the coated and non-coated gloves do not have acceptable donning characteristics with respect to damp and wet skin, which is one of the critical product requirements for surgical glove applications. Furthermore, in the case of laminated rubber gloves, the laminates or coatings can easily crack and expose the wearer to the base natural rubber polymer used to construct the glove. Finally, some of these gloves also exhibit self-sticking between the inner glove surfaces which create difficulties for health care workers trying to don the gloves in a sterile environment.

The majority of commercially available powder-free latex gloves are manufactured by first preparing a powdered glove on-line and then removing the powder from the glove by chlorination and rinsing off-line. The chlorination process oxidizes the surface of the glove thereby providing improved dry donning characteristics. Chlorination also removes any powder deposited on the gloves during the rinsing operation. The chlorination process is generally rapid, which in turn leads to a problem in consistency during the processing step. Variation in processing between batches, between gloves in the same batch, and even between areas on the same glove can lead to differences in surface tack. For example, a single glove may have areas of reduced tack adjacent to areas of increased tack. Conventionally, surface tack describes the adherence of an article to itself or an identical article, whereas stickiness is used to describe the adherence of an article to other materials.

Accordingly, there exists a need for improved manufacturing processes for making powder-free elastomeric articles with consistency in surface tack between areas within a single article, between articles processed together, and between articles processed in separate batches.

SUMMARY OF THE INVENTION

The present invention provides a powder-free, natural rubber or synthetic elastomeric article for medical and industrial applications which has consistent surface tack. The elastomeric articles of the invention include medical gloves where the outer surface of the glove is modified to provide improved outer-surface properties. Gloves according to the invention have good donning characteristics and good grippability, as measured by the coefficient of friction of the donning and gripping surfaces.

With respect to medical gloves, the gloves may be inner-nitrile rubber coated, where the inner coating on the gloves of the invention is a cross-linked nitrile rubber blended with a silicone. Interposed between the nitrile rubber coating and the elastomeric glove is an intermediate layer of a rubber blend comprised of natural or synthetic rubber and nitrile rubber. Comparative testing demonstrates that such inventive gloves have improved adhesion between the coating and the base glove as compared to those coated gloves which do not contain the intermediate layer of rubber blend.

The inventive gloves have a unique surface texture which improves the outer-surface properties of the gloves. The gloves of the invention also exhibit good donning with respect to both dry and wet skin. The improved outer-surface properties are preferably reflected in a reduction of variation in outer-surface tack between different gloves and in outer-surface tack of a single glove as compared to untreated gloves.

The present invention also provides a method of improving the outer-surface properties of gloves that have been chlorinated comprising the steps of chlorinating the surface of gloves followed by treating the inner and/or outer surface of the chlorinated gloves with an aqueous mixture of silicone emulsion and ammonium salts of alkyl phosphates wherein the gloves contain an elastomeric layer. The elastomeric layer is preferably natural rubber latex, synthetic polyisoprene, nitrile, or blends thereof.

PREFERRED EMBODIMENTS OF THE INVENTION

The type of elastomeric article of the invention is not limited, but preferably is powder-free and can be a glove, a condom, a stent, a catheter balloon, a probe cover, or another elastomeric device. In the case of medical gloves, preferably the gloves are comprised of a natural rubber latex, nitrile, polybutadiene, polyvinylchloride, polyurethane, synthetic polyisoprene, styrene diblock and triblock copolymers, or other synthetic elastomers, including blends thereof. Some gloves that can serve as starting materials for surface modification include those described in U.S. Pat. Nos. 6,391,409, and 6,195,805. For example, U.S. Pat. No. 6,391,409 describes powder-free nitrile coated gloves with an intermediate rubber-nitrile layer between the glove and the coating. Additionally, U.S. Pat. No. 6,195,805 describes powder-free surgical gloves. U.S. Pat. Application Publication 2002/0173563 describes polyisoprene articles made by a process comprising an accelerator composition. The above publications are incorporated by reference in their entirety.

The natural rubber used to form a base glove may be compounded with stabilizers, a crosslinker, a vulcanization activator, a vulcanization accelerator, an antioxidant, an antiozonant and optionally, white or other colored pigments.

A preferred embodiment of the invention includes a powder-free elastomeric glove having an internal surface comprising a first elastomeric layer, a second intermediate layer of a rubber blend comprised of a synthetic rubber and nitrile rubber disposed on said first layer and a third nitrile rubber coating layer disposed on said intermediate layer, and wherein the glove has an outer surface layer comprising a mixture of silicone and ammonium salts of alkyl phosphates. In a particularly preferred embodiment, the first elastomeric layer is a natural rubber, nitrile, or synthetic polyisoprene layer. An especially preferred embodiment has the same synthetic rubber in the elastomeric layer and as part of the rubber blend in the intermediate layer. In an additional embodiment, the nitrile rubber is comprised of a carboxylated acrylonitrile butadiene rubber having an acrylonitrile content of about 25 to about 40 parts, a butadiene content of about 55 to about 68 parts and a carboxylic acid content of about 3 to about 6 parts.

Other embodiments of the invention include a glove comprising a polyisoprene layer and having a tensile strength of greater than 3000 psi as measured in accordance with ASTM D412, said glove being prepared from a polyisoprene latex composition comprising a dithiocarbamate compound, a thiazole compound, and a guanidine compound, wherein the glove is substantially free of powder, and further wherein the glove has an outer surface layer comprising a mixture of silicone and ammonium salts of alkyl phosphates.

In addition to the articles themselves, the invention includes a method of obtaining the elastomeric articles and a method of improving the outer surface properties of elastomeric articles, including gloves, that have been chlorinated comprising the steps of obtaining the elastomeric article and chlorinating its surfaces, followed by treating the surfaces of the chlorinated article with an aqueous mixture of silicone emulsion and ammonium salts of alkyl phosphates wherein the article contains an elastomeric layer selected from the group consisting of natural rubber latex, synthetic polyisoprene, nitrile, and blends thereof. In the case of powdered gloves, substantially all of the powder can be removed from the inner and/or outer surface, preferably during or following the chlorination step. The improved surface properties include decreased variation in surface tack between different gloves and decreased variation in the surface of a single glove as compared to untreated gloves.

In addition, the invention includes a process for making a powder-free elastomeric glove having an internal surface comprising a first elastomeric layer, a second intermediate layer of a rubber blend comprised of a synthetic rubber and nitrile rubber disposed on the first layer and a third nitrile rubber coating disposed on said intermediate layer, and wherein the glove has an outer-surface modification treatment comprising a mixture of silicone and ammonium salts of alkyl phosphates, comprising the steps of: (a) dipping a former into a coagulant dispersion to deposit a coagulant layer on the former; (b) dipping the former with the deposited coagulant layer into an elastomer to produce a second layer comprising coagulated elastomeric layer thereon; (c) dipping the second layer of coagulated elastomer into a blend of a synthetic rubber and a nitrile rubber dispersion to form an intermediate layer on the glove; (d) dipping the intermediate layer of a synthetic rubber and a nitrile rubber into a powder-free dispersion comprised of a nitrile rubber dispersion and a silicone emulsion; (e) curing the layers and the coating on the former; (f) stripping the glove from the former; (g) turning the glove so that the coated side of the article is on the exterior of the glove; (h) treating the glove to remove powder; (i) treating the surfaces of the glove with a solution comprising an aqueous mixture of silicone emulsion and ammonium salts of alkyl phosphates; (j) drying the glove; (k) turning the glove so that the coated side of the glove is on the interior of the glove; and (l) drying the glove. Alternately, step (i) can be performed between steps (k) and (l) as a treatment of the outer surface rather than immediately following step (h). Preferably, the powder is removed from the glove by immersing the glove into an aqueous chlorinating solution followed by the step of rinsing the glove. A preferred process involves a step of leaching the glove in water. A particularly preferred embodiment includes cetylpyridinium chloride in the surface treatment.

The current invention is directed to a surface modification treatment in the process of making elastomeric articles. The surface modification treatment comprises a chlorination step to remove powder, followed by treatment with an aqueous mixture of silicone emulsion and ammonium salts of alkyl phosphates. The silicone emulsion is a siloxane based silicone emulsion. Preferably, the silicone is a poly(alkylsubstituted)siloxane emulsion. Most preferably, the silicone emulsion is a polydimethylsiloxane emulsion. One such suitable silicone emulsion is available under the name SM2140, which includes water, polydimethylsiloxane, nonoxynol-20, and laureth-23. Ammonium salts of alkyl phosphates are commercially available under the name DARVAN L. Ammonium salts of alkyl phosphates include $C_{12}$-$C_{22}$ alkyl groups. Additional ingredients in the surface modification treatment include cationic film-formers, fixative polymers, lubricants, and other suitable ingredients such as antifoam agents.

Synthetic diene based elastomers used to form the base glove such as polybutadiene, synthetic polyisoprene, nitrile, and blends thereof can be compounded with similar compounding ingredients as set forth above. Other synthetic thermoplastic elastomeric materials used for the base glove such as polyvinylchloride, polyurethanes, styrene diblock and triblock copolymers and blends thereof do not require crosslinking to prepare a glove with the desired physical properties. Accordingly, these synthetic elastomers may be compounded with stabilizers, crosslinkers, vulcanization activators and accelerators, antioxidants, antiozonants and color pigments as described below.

Suitable stabilizers include oleates, stearates, alginates, polyacrylates, xanthan gums, caseinates or other nonionic and ionic surfactants. Typical crosslinkers which may be used in the compounding formulation include sulfur or other organic peroxides. Suitable vulcanization activators include metal oxides, such as magnesium oxide, lead oxide, and preferably, zinc oxide. The vulcanization accelerator may be chosen from mercaptobenzothiazoles and their derivatives, dithiocarbamates and their derivatives, sulfur donors, guanidines and aldehyde-amine reaction products. Suitable antioxidants include hindered arylamines or polymeric hindered phenols. Typical antiozonants which may be used in the compounding formulation include paraffinic waxes, microcrystalline waxes and intermediate types of waxes (which are blends of both paraffinic and microcrystalline waxes). Typical white pigments that may be used include titanium dioxide and zinc oxide.

Lubricants may preferably be included in the surface modification treatment to improve donning characteristics. Suitable lubricants that may be used to provide wet and damp donning characteristics are nonionic and ionic surfactants. Among these surfactants, the cationic and amphoteric surfactants are most preferred for these applications. One suitable lubricant is cetylpyridinium chloride (CPC). These surfactants may also be combined with other lubricants such as silicones, stearates, or other water soluble polymers such as chitosan, polyethylene oxide or polyvinyl alcohol, to provide acceptable donning features for surgical glove applications. Antifoam agents may preferably be included in the surface modification treatment. A preferred antifoam agent is the commercially available ANTIFOAM 1920.

Those skilled in the art will readily be able to vary the compounding ingredients in the formulation process to suit the particular elastomers used to form the base glove as well as the final article desired.

As noted above, the gloves fabricated in accordance with the present invention may be prepared as known in the art. For example, U.S. Pat. No. 6,391,409 describes powder-free nitrile coated gloves with an intermediate rubber-nitrile layer between the glove and the coating. U.S. Pat. Application Publication 2002/0173563 describes polyisoprene articles made by a process comprising an accelerator composition.

To prepare the powder free gloves, the gloves are post-processed by chlorination as follows. The coated gloves are initially turned inside out with the coated surfaces on the outside of the gloves. The gloves are optionally pre-rinsed with water two times (for about 2.5 minutes per time) and immersed in an aqueous chlorinating solution in a chlorinator for about at least 6 minutes. The chlorine concentration may vary from about 100 ppm to about 1500 ppm. Preferably the chlorine concentration is about 150 to about 700 ppm. Most preferably, the chlorine concentration is about 250 ppm to about 350 ppm. After chlorination, the chlorinating solution is neutralized by adding a base (e.g., sodium hydroxide or ammonium hydroxide) to the solution and the gloves are then tumbled for about 4 minutes or until the pH of the solution is about 7 or above. The neutralized solution is then drained and the gloves are rinsed with water for about 2.5 minutes. The gloves may be rinsed three more times (for about 2.5 minutes per time) to remove any residual chemicals. The gloves are extracted to remove excess water and a post-treatment solution is then applied to the coating surface, e.g., by spraying or by tumbling. The post-treatment solution is preferably comprised of about 0.1 wt % to about 3 wt % ammonium salts of alkyl phosphates, about 0.3 wt % to about 2 wt. % cetylpyridinium chloride, and about 0.10 wt % to about 1 wt. % silicone emulsion. Preferably, the post-rinsing treatment further comprises an antifoam agent. The gloves are tumbled until the post-rinsing treatment is complete, preferably about 15 minutes. After the post-treatment application, the gloves are dried at about 55° C. for about 20 minutes. The treated gloves are turned outside-in with the coated surfaces on the inside of the gloves. The treated gloves are then dried.

The surface modification treatment involves application to the coating surface, e.g. by spraying or by tumbling. During this treatment, the gloves can be in two different configurations-non-inverted or inverted with respect to the final donning surface. The surface modification treatment can be applied by direct treatment on the exposed surface of the glove or by indirect treatment of the non-exposed surface through the opening in the cuff. The application can be in two steps, where the treatment is applied directly to a surface, followed by inversion and direct application to the other surface. Alternatively, the surface modification treatment can be applied directly to the exposed surface and indirectly to the non-exposed surface in a single step. For the method where the surface modification treatment is applied by spraying, a preferred embodiment involves spraying a combination of cetylpyridinium chloride, DARVAN L, and SM2140 on the donning side of an inverted glove, drying and inverting, and further spraying of a combination of DARVAN L and SM2140 on the outer surface.

For medical, examination and industrial applications, the powder-free gloves of the invention can be prepared as set forth above except the chlorination processing steps are modified as follows. After stripping from the former, the coated gloves are optionally pre-rinsed with water and immersed in an aqueous chlorinating solution in a chlorinator for at least about 6 minutes. The chlorine concentration may vary from about 100 ppm to about 1500 ppm. Preferably, the chlorine concentration is about 150 to about 700 ppm. Most preferably, the chlorine concentration is about 250 ppm to about 350 ppm. After chlorination, the chlorinating solution is neutralized by adding a base to the solution and the gloves are then tumbled for about 4 minutes or until the pH of the solution is about 7 or above. The neutralized solution is then drained and the gloves are rinsed with water for about 2.5 minutes. The gloves are then rinsed three more times to remove any residual chemicals. After rinsing, the gloves are dried at about 55° C. for at least 20 minutes or until the gloves are dried. The gloves are extracted to remove excess water and a post-treatment solution is then applied to the coating surface, e.g., by spraying or by tumbling. The post-treatment solution is preferably comprised of about 0.1 wt % to about 3 wt % ammonium salts of alkyl phosphates, about 0.3 wt % to about 2 wt. % cetylpyridinium chloride, and about 0.10 wt % to about 1 wt. % silicone emulsion. Preferably, the post-rinsing treatment further comprises an antifoam agent. The gloves are tumbled until the post-rinsing treatment is complete, preferably about 15 minutes. After the post-treatment application, the gloves are dried at about 55° C. for about 20 minutes. The powder-free gloves are now ready for packing. Preferably, the above described post-processing steps are suitable for processing a glove with a bead on the cuff. The beading step can be applied before or after dipping of the former with the intermediate rubber blend layer into the powder-free nitrile rubber dispersion as described above.

The finished gloves are packaged and may be sent for sterilization by gamma or electron beam radiation. The gloves of the invention have a thickness of at least about 0.003 inches. Preferably, the thickness of the gloves ranges between about 0.004 inches and about 0.012 inches. Most preferably, the glove thickness is between about 0.005 and about 0.009 inches. The glove thickness is measured by a digital thickness gauge and is the average of three measurements in the palm area. Dry kinetic COF is measured according to ASTM D1894.

The surface-modified gloves according to the invention have decreased variation in outer-surface tack between different gloves and decreased variation in outer-surface tack along the outer surface of a single glove as compared to untreated gloves. The benefits of such decreased variation include improved reliability in, for example, handling surgical instruments. Additional benefits include improved efficiency in donning gloves, decreased waste in disposing of irregular gloves or gloves with mismatched tack levels, minimized internal and external stickiness, reduced variation in surface grip, improved double-donning, and overall softer feel. Furthermore, the gloves have a subjectively softer feel. The treatment is effective for gloves with an internal coating as well as without an internal coating and is applicable to gloves made of natural rubber, synthetic polyisoprene rubber, nitrile rubber, and blends thereof.

While the surface modification treatment of the present invention is directed mainly at the external (patient) surface of the gloves, it may be convenient and economical to incorporate a mixture of ammonium salts of alkyl phosphates and silicone emulsion with a lubricant such as cetylpyridinium chloride in a one-step treatment by tumbling the gloves with the donning surface facing outside directly in contact with the post-chlorination mixture. While in this configuration, the patient side of the glove is contacted with the surface modification treatment through the opening at the cuff. The mixture is preferably comprised of about 0.1 wt % to about 3 wt % ammonium salts of alkyl phosphates, about 0.3 wt % to about 2 wt % cetylpyridinium chloride, and about 0.1 wt % to about 1 wt % silicone emulsion. Preferably, the mixture further comprises an antifoam agent. After completion of tumbling, the gloves are partially dried and manually inverted so that the donning surface is now on the inside and the gloves are further dried before packing. When the post-treatment is by spraying, the post-treatment mixture is sprayed directly onto the donning surface of the gloves. If the amount of treatment mixture is insufficient to give the desired surface modification on acne patient side of the gloves due to limited access through the opening at the cuff, a second spraying treatment is carried out after the gloves are partially dried and manually inverted to expose the patient side facing outside. For this second spraying, the post-treatment mixture is preferably comprised of about 0.1 wt % to about 3 wt % ammonium salts of alkyl phosphates and about 0.1 wt % to about 1 wt % silicone. After completion of this second spraying, the gloves are dried and ready for packing.

The invention is further illustrated by the following examples. The Comparative Examples that follow describe the formation of gloves according to the prior art. Examples 1-2 add a surface modification treatment according to the invention. Examples 3-5 describe comparisons between surface-modified and unmodified gloves and illustrate the improved properties exhibited by the inventive gloves.

COMPARATIVE EXAMPLE 1

Polyisoprene latex (KRATON IR PR401 lot # 000313 having TSC 64.40% obtained from Shell International Corporation, Houston, Tex.) was diluted with water. Sodium caseinate (obtained from Technical Industries, Inc., Peacedale, R.I.) was then added to the mixture and stirred at ambient temperature. While under continuous stirring, zinc oxide and sulfur dispersions were added to the mixture. Accelerator compounds ZDEC (from Akron Dispersions, Akron Ohio), ZMBT, and DPG (from Akron Dispersions, Akron, Ohio) were formulated into dispersions and then added. WINGSTAY L was added and the mixture was stirred for approximately 15 minutes. The composition was diluted to about 37.0% solids with water. The pH was adjusted using ammonium hydroxide to pH 10.7. The composition was maintained at a temperature of 25° C. and stored under continuous agitation for 24 hours at a temperature of less than 25° C.

Accordingly, the following is a summary of the formulation ingredients and their respective amounts. All percentages are percentages by weight unless otherwise noted.

| Formula 1: | |
| --- | --- |
| Ingredient | Parts (phr) dry weight |
| Polyisoprene | 100.00 |
| ZDEC | 0.50 |
| ZMBT | 0.50 |
| DPG | 1.00 |
| Sodium caseinate | 0.75 |
| ZnO | 0.50 |
| Sulfur | 1.25 |
| WINGSTAY L | 2.00 |

A glove former was preheated to 100° C. in an oven, removed and dipped into a coagulant composed of soft water 80.65%, calcium nitrate 13.65%, calcium carbonate 5.46%, wetting agent (SURFONYL TG 0.2%), cellulose (CELLOSIZE QP 52000) 0.04%) at a temperature of 56° C. for a period of 30 seconds and removed. The coagulant-coated former was cooled to a temperature of about 58° C. and was placed in a drying oven at a temperature of 100° C. for a period of time sufficient to dry the coagulant.

The coagulant-coated former was removed from the oven and dipped into the compounded polyisoprene latex composition of Formula I at a temperature of 250° C. for a period of 0.8 minutes. The coated former was removed and placed into a pre-heated oven at a temperature of 130° C. for a period of 0.8 minutes.

The coated former was then removed from the oven and placed into water leaching tank at a temperature of 50° C. for a period of 5.0 minutes. The former was removed from the leaching tank and placed into an oven at a temperature of 70° C. for 30 seconds.

The former was removed from the oven and dipped into a silicone tank at a temperature of 40° C. for 30 seconds. The former was removed from the silicone tank and while still on the former, the glove was beaded at the cuff using a beader roller.

The former was then placed into a second stage cure oven and moved at zone temperatures ranging from 110° C. to 135° C. for a total time period lasting for a period of 9.5 minutes. After exiting the curing oven, the glove was subjected to a post-cure leaching. At this step, the glove on the former was rinsed with water at a temperature of 70° C. water for a period of about 1 minute.

The glove was placed in a slurry tank at a temperature of 55° C. for 30 seconds. The slurry composition contained 85.2% water, 14.33% starch, 0.4% cellulose (CELLOSIZE QP 52000), 0.4% sodium hypochlorite, 0.01% surfactant (DARVAN) and 0.02% CASASTAB T. The formers were then placed into a post-slurry oven to dry the glove thereby producing the final glove. The glove covered former was cooled and the glove was stripped therefrom.

The physical properties of the glove produced by the above process were evaluated. Samples were obtained from the gloves exhibited average tensile strength values of 3810 psi, tensile modulus value of 171 psi at 300% elongation, and 1125% elongation at break as measured using ASTM D142.

COMPARATIVE EXAMPLE 2

A powder-free nitrile-coated natural rubber latex glove with an intermediate natural rubber-nitrile layer between the glove and the nitrile coating was prepared as follows. Glove formers were pre-heated to about 65° C. in an oven for about 5 minutes. The preheated former then was dipped into a stirred, water based coagulant suspension maintained at a temperature between about 55° C. to about 60° C. The coagulant-dipped former was then returned to the heated oven for about 5 minutes to dry the coagulant layer.

The coagulant-coated former was dipped into a compounded natural rubber latex for a time sufficient to produce the desired glove thickness. The natural rubber latex was compounded with stabilizers, crosslinker, vulcanization activator, vulcanization accelerators, antioxidant, antiozonant and white pigment. The solid content of the compounded latex was about 38 wt. %. The former bearing the coagulated latex was then removed from the compounded natural rubber latex and immediately dipped into a second rubber blend latex for about 13 to about 15 seconds. The rubber blend latex comprised about 2.3% compounded natural rubber latex and about 2.3% of carboxylated acrylonitrile butadiene latex and about 95.4% water. The formulation of the compounded natural rubber latex used in this rubber blend latex was the same as the one used in the first latex dipping. The ratio of acrylonitrile/butadienelcarboxylic acid for the nitrile rubber was 39/58/3.

The former was removed from the second rubber blend latex and dried in a heated oven at about 58° C. The coagulated latex layer was leached in water maintained at about 55° C. to about 80° C. for about 5 minutes. The former was then dipped into a compounded nitrile blend latex with a total solid content of about 5% to form a coating on the intermediate natural rubber-nitrile blend layer. The nitrile blend was comprised of a 50/50 blend of two carboxylated acrylonitrile butadiene rubber latices with two different acrylonitrile/butadiene/carboxylic acid ratios 39/58/3 and 39/55/6. The nitrile blend latex was further compounded with 1 part of sulfur dispersion (crosslinker), 1 part of ZDBC dispersion (vulcanization accelerator), 3 parts of ZnO dispersion (vulcanization activator) and 15 parts of silicone emulsion (SM 2140 obtained from General Electric). The dwell time for the coating dipping was about 13 to about 15 seconds.

The cuff of the coated glove was beaded by a beader and the former was placed in an oven maintained at about 125° C. for about 20 minutes in order to cure the glove. The former bearing the glove was then removed from the oven and allowed to cool. The glove was then stripped from the former.

The glove was then post-processed by chlorination. First, the coated glove was turned inside out manually and loaded into a chlorinator. The glove was pre-rinsed 2 times for a total time of about 5 minutes. An aqueous chlorine solution of about 300 ppm chlorine was added to the chlorinator and the gloves tumbled for about 8.3 minutes. The chlorinating solution was then neutralized with 50% sodium hydroxide solution for about 4 minutes. The glove was post-rinsed 4 times for a total time of about 10 minutes. The glove was then transferred to a tumbling washer for the lubrication process. Excess water was removed from the glove by spinning the glove for about 2 minutes. The washer was then filled with an aqueous lubrication solution comprised of about 0.5 wt % of cetylpyridinium chloride and 0.15 wt % of silicone emulsion. The glove was tumbled in the lubrication solution for about 5 minutes. The lubrication solution was drained and the glove was tumbled for an additional 5 minutes. The glove was then removed from the tumbler washer and dried in a dryer with a heating cycle of about 20 minutes at about 55° C. and a cool down cycle for about 10 minutes. The glove was removed from the dryer and turned inside out manually. The glove was dried again in the dryer at about 50° C. for about 5 minutes and allowed to cool down to room temperature for about 5 minutes.

The physical properties of the powder-free coated glove prepared as set forth were measured according to ASTM D412-92. The gloves had a tensile strength of 4323 psi, a tensile stress at 500% of 313 psi, and an ultimate elongation of 1022%. The coefficient of friction (COF) of both the outside and inside surfaces in the palm area of the glove were measured according to ASTM D1894-95. The static and kinetic COF for the inside surface were 0.72 and 0.46, respectively. The static and kinetic COF for the outside surface were 1.22 and 1.61, respectively.

The donning characteristics of the glove were evaluated qualitatively with respect to damp skin on a scale of 1 to 5, 1 being the worst with extreme difficulties in donning the glove and 5 being the best with extreme ease in donning the glove. This determination was made by having the glove donned by a person with damp skin. The glove dons extremely well with respect to damp and wet skin with a rating of 5.

The adhesion of the coating was also evaluated qualitatively. In this test, the coated glove surface was stretched to more than 500% and the coating was rubbed repeatedly using the thumb. The coated surface was then visually examined for coating flakes and powdery substance. The adhesion of the coating was rated qualitatively on a scale of 1 to 5, 1 being the worst with the entire coating flaking off the rubber substrate and 5 being the best with no visual appearance of powdery substance on the surface of the glove. Using this test, the adhesion of the inventive coating is quite good with a rating of 5 on a scale of 1 to 5, i.e., no flaking or shedding of the powder was observed after stretching the glove to about 500% and rubbing it repeatedly with the thumb.

EXAMPLE 1

The unmodified gloves were prepared in the manner of Comparative Example 1. To prepare the powder-free gloves, the gloves were post-processed by chlorination as follows. The coated gloves were initially turned inside out with the coated surfaces on the outside of the gloves. The gloves were pre-rinsed with water two times (for about 2.5 minutes per time) and immersed in an aqueous chlorinating solution in a chlorinator for about at least 6 minutes. After chlorination, the chlorinating solution was neutralized by adding a base (e.g., sodium hydroxide or ammonium hydroxide) to the solution and the gloves were then tumbled for about 4 minutes or until the pH of the solution was about 7 or above. The neutralized solution was then drained and the gloves were rinsed with water for about 2.5 minutes. The gloves were rinsed three more times (for about 2.5 minutes per time) to remove any residual chemicals. The gloves were extracted to remove excess water and a surface modification treatment solution was then applied to the coating surface, e.g., by spraying or by tumbling. The surface modification treatment solution was comprised of about 0.1 wt % to about 3 wt % ammonium salts of alkyl phosphates, about 0.3 wt % to about 0.2 wt. % cetylpyridinium chloride, and about 0.10 wt % to about 1 wt. % silicone emulsion. The gloves were tumbled until the surface modification treatment was complete, preferably about 15 minutes. After the surface modification treatment, the gloves were dried at about 55° C. for about 20 minutes. The gloves were then turned inside out and dried at about 55° C. for about 15 minutes.

EXAMPLE 2

The unmodified gloves were prepared in the manner of Comparative Example 2. To prepare the powder-free gloves, the gloves were post-processed by chlorination as follows. The coated gloves were initially turned inside out with the coated surfaces on the outside of the gloves. The gloves were pre-rinsed with water two times (for about 2.5 minutes per time) and immersed in an aqueous chlorinating solution in a chlorinator for about at least 6 minutes. After chlorination, the chlorinating solution was neutralized by adding a base (e.g., sodium hydroxide or ammonium hydroxide) to the solution and the gloves were then tumbled for about 4 minutes or until the pH of the solution was about 7 or above. The neutralized solution was then drained and the gloves were rinsed with water for about 2.5 minutes. The gloves were rinsed three more times (for about 2.5 minutes per time) to remove any residual chemicals. The gloves were extracted to remove excess water and a post-treatment solution was then applied to the coating surface, e.g., by spraying or by tumbling. The surface modification treatment solution was comprised of about 0.1 wt % to about 3 wt % ammonium salts of alkyl phosphates, about 0.3 wt % to about 2 wt. % cetylpyridinium chloride, and about 0.10 wt % to about 1 wt. % silicone emulsion. The gloves were tumbled until the surface modification treatment was complete, preferably about 15 minutes. After the surface modification treatment, the gloves were dried at about 55° C. for about 20 minutes. The gloves were then turned inside out and dried at about 55° C. for about 15 minutes.

EXAMPLE 3

Examples 3-5 compare the surface properties of gloves with and without surface treatments according to the invention. The surface treatments according to the present invention reduce surface grip (i.e. surface friction) and variability of surface grip as determined by standard deviation of the coefficient of friction (COF) as measured by the COF of the external surface of the thumb sliding against the external surface of the index finger using a Plint friction test machine. (SMT=Surface-Modification Treatment)

| COF | ¹Comparative Example 1 | ²Example 1 |
|---|---|---|
| Average | 0.39 | 0.34 |
| Standard Deviation | 0.05 | 0.04 |

¹Esteem ® by Allegiance Healthcare Corporation
²Esteem ® SMT by Allegiance Healthcare Corporation

| COF | ¹Comparative Example 2 | ²Example 2 |
|---|---|---|
| Average | 0.53 | 0.37 |
| Standard Deviation | 0.12 | 0.09 |

¹Protegrity ® by Allegiance Healthcare Corporation
²Protegrity ® SMT by Allegiance Healthcare Corporation

EXAMPLE 4

The treatment reduces internal sticking as qualitatively assessed using a 1 to 5 scale, where 1=no stickiness to cuff, 3=moderate stickiness to cuff, and 5=serious stickiness to cuff.

| | ¹Comparative Example 1 | ²Example 1 |
|---|---|---|
| Average | 2 | 1 |

¹Esteem ® by Allegiance Healthcare Corporation
²Esteem ® SMT by Allegiance Healthcare Corporation

EXAMPLE 5

The treatment reduces sticky cuff as qualitatively assessed using a 1 to 5 scale, where 1=no stickiness to cuff, 3=moderate stickiness to cuff, and 5=serious stickiness to cuff.

| | ¹Comparative Example 2 | ²Example 2 |
|---|---|---|
| Average | 3 | 1 |

¹Protegrity ® by Allegiance Healthcare Corporation
²Protegrity ® SMT by Allegiance Healthcare Corporation The foregoing description and examples relate only to preferred embodiments of the present invention and numerous changes and modifications may be made therein without departing from the spirit and scope of the invention as defined in the following claims. For example, the invention is not limited to gloves, but rather encompasses any elastomeric article, in particular gloves, stents, condoms, and probe covers. The invention further encompasses methods of obtaining elastomeric articles comprising the steps of forming an elastomeric article, treating the surface of the article with chlorine, removing substantially all powder from the surface of the article, and treating the surfaces of the article with a surface modification treatment comprising an aqueous mixture of silicone emulsion and ammonium salts of alkyl phosphates.

What is claimed is:

1. A glove, comprising:
   an inner skin-contacting surface; and
   an outer surface comprised of an elastomeric material,
   wherein said elastomeric material comprises a polymer selected from the group consisting of natural rubber latex, synthetic polyisoprene, nitrile, and blends thereof,
   wherein said outer surface is coated with a composition comprising a mixture of silicone, ammonium salts of alkyl phosphates, and cetyl pyridinium chloride, and
   wherein the glove has a reduced coefficient of friction compared to the same glove without said outer surface coating composition.

2. The glove of claim 1, wherein the glove is powder free.

3. The glove of claim 2, wherein the elastomeric material is a natural rubber latex.

4. The glove of claim 2, wherein the elastomeric material is polyisoprene.

5. The glove of claim 2, wherein the elastomeric material is nitrile.

6. The glove of claim 2, wherein the elastomeric material is a blend of two or more polymers selected from the group consisting of natural rubber latex, synthetic polyisoprene, and nitrile.

7. The glove of claim 1, wherein the silicone comprises polydimethylsiloxane.

8. The glove of claim 1, wherein said coated outer surface of the glove has a coefficient of friction less than about 0.4.

9. The glove of claim 1, wherein the glove has reduced stickiness when compared to the same glove without said outer coating composition.

10. The glove of claim 1, wherein the glove has improved double-donnability as measured by the coefficient of friction when compared to the same glove without said outer surface coating composition.

11. The glove of claim 1, further comprising an intermediate layer disposed on said inner skin-contacting surface.

12. The glove of claim 11, wherein said intermediate layer comprises a blend of synthetic rubber and nitrile rubber.

* * * * *

UNITED STATES PATENT AND TRADEMARK OFFICE
CERTIFICATE OF CORRECTION

| | | |
|---|---|---|
| PATENT NO. | : 8,062,755 B2 | Page 1 of 1 |
| APPLICATION NO. | : 12/487293 | |
| DATED | : November 22, 2011 | |
| INVENTOR(S) | : Seong Fong Chen et al. | |

It is certified that error appears in the above-identified patent and that said Letters Patent is hereby corrected as shown below:

On the Title Page, second Inventor's name should read:

--<u>Chuang</u> Sim Chong--

Signed and Sealed this
Twenty-seventh Day of March, 2012

David J. Kappos
*Director of the United States Patent and Trademark Office*